US008035816B2

(12) United States Patent
Randow et al.

(10) Patent No.: US 8,035,816 B2
(45) Date of Patent: Oct. 11, 2011

(54) METHOD AND APPARATUS FOR MEASURING THE OPTICAL ABSORPTION OF SAMPLES

(75) Inventors: Albert Randow, Bruchkoebel (DE); Helmut Dandl, Eichstaett (DE); Hans Krause, Bad Nauheim (DE)

(73) Assignee: Emerson Process Management GmbH & Co. OHG, Wessling (DE)

( * ) Notice: Subject to any disclaimer, the term of this patent is extended or adjusted under 35 U.S.C. 154(b) by 407 days.

(21) Appl. No.: 12/295,845

(22) PCT Filed: Apr. 10, 2007

(86) PCT No.: PCT/EP2007/053476
§ 371 (c)(1),
(2), (4) Date: Oct. 2, 2008

(87) PCT Pub. No.: WO2007/116066
PCT Pub. Date: Oct. 18, 2007

(65) Prior Publication Data
US 2009/0168064 A1 Jul. 2, 2009

(30) Foreign Application Priority Data
Apr. 7, 2006 (DE) .......................... 10 2006 016 855

(51) Int. Cl.
*G01N 21/59* (2006.01)
(52) U.S. Cl. .................... 356/343; 356/432; 356/435
(58) Field of Classification Search .......... 356/432–442; 250/343, 458.1, 459.1, 461.1, 461.2
See application file for complete search history.

(56) References Cited

U.S. PATENT DOCUMENTS

| 3,790,797 | A | * | 2/1974 | Sternberg et al. | 250/345 |
| 4,008,394 | A | | 2/1977 | Risgin et al. | |
| 4,101,221 | A | | 7/1978 | Schunck et al. | |
| 4,305,664 | A | * | 12/1981 | Akitomo | 356/323 |
| 4,492,862 | A | * | 1/1985 | Grynberg et al. | 250/255 |
| 4,565,447 | A | * | 1/1986 | Nelson | 356/319 |
| 4,577,966 | A | * | 3/1986 | Fukasawa | 356/325 |
| 4,737,652 | A | * | 4/1988 | Faschingleitner et al. | 250/575 |

(Continued)

FOREIGN PATENT DOCUMENTS
DE 26 14 181 C3 10/1977
(Continued)

*Primary Examiner* — Sang Nguyen
(74) *Attorney, Agent, or Firm* — Arent Fox LLP

(57) ABSTRACT

In a method and apparatus for measuring the optical absorption of samples having a light source (1), a photoelectric converter (8), a measurement beam path extending between the light source (1) and the converter (8), in which path the sample to be examined is arranged, a reference beam path extending between the light source (1) and the converter (8), in which path a reference sample is arranged, and a motor-driven chopper disc (10), the chopper disc (10) is configured with a first number of first openings (15) unblocking only the measurement beam path and a second number of second openings (16) unblocking only the path for the reference beam. A lock-in amplifier (21) and a device (17) for synchronising the lock-in amplifier (21) with the chopper disc (10) is connected to the converter (8) and an evaluation circuit (26) establishes the quotient of the transmitted intensity of the reference beam path detected by the converter (8) and the transmitted intensity of the measurement beam path detected by the converter (8) as a measurement for the concentration of the sample in such a way that the decrease in the intensity of the beam by absorption leads to an increase in sensitivity.

13 Claims, 2 Drawing Sheets

U.S. PATENT DOCUMENTS

Figure 1:
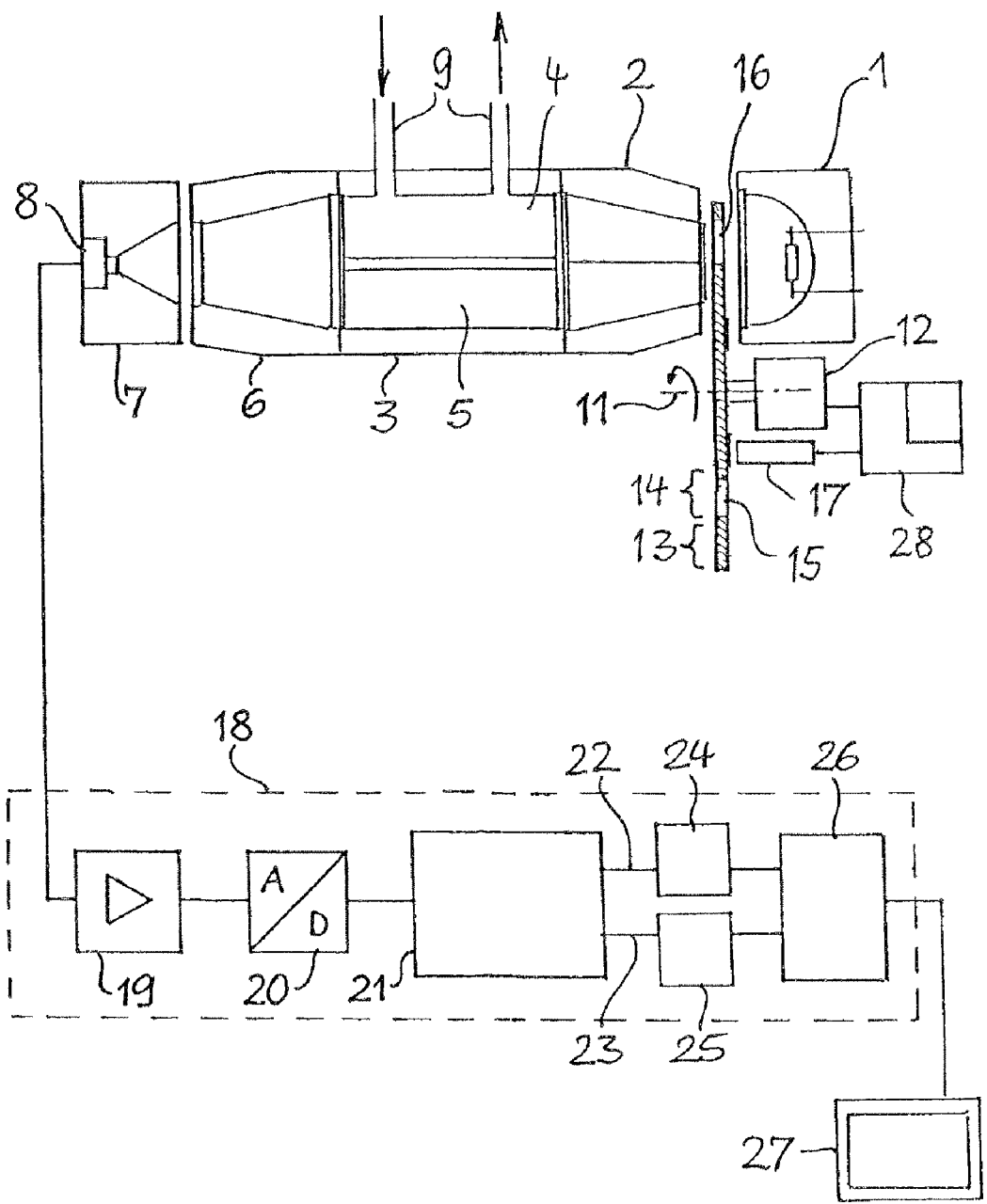

| | | | |
|---|---|---|---|
| 4,937,448 A * | 6/1990 | Mantz et al. | 250/343 |
| 5,026,991 A * | 6/1991 | Goldstein et al. | 250/343 |
| 5,317,156 A * | 5/1994 | Cooper et al. | 250/345 |
| 5,457,320 A * | 10/1995 | Eckles et al. | 250/345 |
| 5,515,859 A * | 5/1996 | Paz | 250/339.13 |
| 5,677,534 A * | 10/1997 | Araya | 250/345 |
| 5,930,000 A * | 7/1999 | Brand | 356/437 |
| 6,040,915 A * | 3/2000 | Wu et al. | 356/435 |
| 6,636,316 B1 * | 10/2003 | Matsumoto et al. | 356/437 |
| 6,775,001 B2 * | 8/2004 | Friberg et al. | 356/437 |
| 7,251,034 B2 * | 7/2007 | Kluczynski et al. | 356/437 |
| 7,336,362 B2 * | 2/2008 | Van Geen | 356/407 |
| 2004/0051043 A1 | 3/2004 | Kilian et al. | |

FOREIGN PATENT DOCUMENTS

| | | |
|---|---|---|
| DE | 234928 A1 | 4/1986 |
| DE | 197 51 819 A1 | 5/1999 |
| DE | 100 62 126 A1 | 6/2002 |
| EP | 0 290 657 A1 | 11/1988 |

* cited by examiner

METHOD AND APPARATUS FOR MEASURING THE OPTICAL ABSORPTION OF SAMPLES

The invention relates to a method for measuring the optical absorption of samples, in which light from a radiation source is periodically directed at a sample to be examined and a reference sample and the transmitted radiation intensity is converted into an electrical measurement signal and into an electrical reference signal via a photoelectric converter. The invention further relates to an apparatus for measuring the optical absorption of samples having a light source, a photoelectric converter, a measurement beam path extending between the light source and the converter, in which path the sample to be examined is arranged, a reference beam path extending between the light source and the converter, in which path a reference sample is arranged, a motor-driven chopper disc with a first number of first openings unblocking only the measurement beam path and a second number of second openings unblocking only the reference beam path and having an evaluation circuit connected to the converter.

A method of the specified type and an apparatus for carrying out the method are known from DE 25 14 181 C3. In this known method, the radiation transmitted from the sample to be examined and the reference sample is alternately directed at the converter and a differential signal is formed from the separate converter signals. Furthermore, the sample and reference sample are irradiated simultaneously during a fraction of a rotation of the chopper disc and are then simultaneously shadowed in such a way that an additional large signal is produced. This large signal is electronically desynchronized and offset with the actual signal. It calibrates and compensates for sensitivity drift of the optical assembly, for example a change in radiation intensity. This known method and apparatus operating in accordance with the method have proven to be effective in practice. However, the method has displayed a particular dependency on temperature and the zero point as well as a considerable linearity error in the measurement signal which increases the costs of processing the signal and impedes signal diagnosis.

The object of the invention is to propose a method of the type mentioned at the outset which is characterised by a particularly low dependency on temperature, a good level of stability at the zero point and a low linearity error in the measurement signal. A further object of the invention is to provide an advantageous apparatus for carrying out the method.

The object is achieved in relation to the method by the features given in claim 1 and in relation to the apparatus by the features disclosed in claim [8]. Advantageous embodiments of the method and the apparatus are disclosed in the sub-claims associated with the said claims respectively.

In the method according to the invention, light from a radiation source is directed at a sample to be examined and at a reference sample, the light transmitting the sample to be examined is modulated with a first frequency and the light transmitting the reference sample is modulated with a second frequency, the transmitted radiation converts the sample to be examined and the reference sample into an electrical mixed signal via a photoelectric converter, the electrical mixed signal is increased, is converted into a digital mixed signal in an analogue-to-digital converter and is separated, with regard to the first frequency, into a measurement signal associated with the sample to be examined and, with regard to the second frequency, into a reference signal associated with the reference sample using a digital lock-in amplifier and the quotient of the reference signal and the measurement signal is formed as a measurement for the concentration of the sample to be examined in such a way that the decrease in radiation intensity due to absorption leads to an increase in sensitivity, resulting in an almost linear response.

The method according to the invention has the advantage that it enables high temperature stability. Changes to the radiation intensity of the beam have a similar effect on the sample and reference sample faces and are offset against one another by the formation of the quotient. The same applies to any influences possibly interfering with signal processing which are eliminated because both signal portions penetrate the same signal processing path. A further advantage of the method according to the invention is a considerably increased linearity of the concentration signal achieved and, in conjunction therewith, a substantial facilitation of signal evaluation. Consequently, for example, $CO_2$ concentration can be determined in all measurement ranges concerned using only two cell lengths. The zero-point stability of the method is also extraordinarily good. It has also been found that the method according to the invention enables high measurement sensitivity and that a rather large dynamic measurement range, for example of 1 to 1,000, can be achieved. Signal evaluation may also take place, for example, by subtraction instead of by the formation of a quotient. However, in this case the advantageous linearity of the concentration signal is not provided to the same degree.

According to a further feature of the invention, it may be provided for temperature-dependent influences on the measurement signal and the reference signal to be separately balanced out for each of the two signals. In this way, temperature influences with a unilateral effect can be taken into consideration. Furthermore, it may be provided for the difference in temperature influences to be balanced out with a temperature-dependent normalisation element which acts only on the measurement signal. Generally, it is therefore desired to keep the temperature path the same on the face of the sample to be examined and on the face of the reference sample by means of suitable structural measures in such a way that measures for balancing out temperature are unnecessary.

According to a further suggestion of the invention, in order to adjust the zero point it is provided for the measurement signal to be configured, when measured with zero test gas on the sample face, by means of a variable correction factor of the evaluation circuit in such a way that the quotient of the measurement and reference signals is one. The zero point is thus determined purely mathematically by subtracting one.

An advantageous apparatus for carrying out the method comprises, according to the invention, a light source, a photoelectric converter, a measurement beam path extending between the light source and the converter, in which path the sample to be examined is arranged, a reference beam path extending between the light source and the converter, in which path a reference sample is arranged, a motor-driven chopper disc with a first number of first openings unblocking only the measurement beam path and a second number, which is different from the first number, of second openings unblocking only the reference beam path, an electronic evaluation circuit connected to the converter which is configured so as to amplify, digitalise and separate converter signals in accordance with two frequencies using a digital lock-in amplifier operating in two frequencies, and so as to form the quotient from a reference signal corresponding to the transmitted intensity of the reference beam path and from a measurement signal corresponding to the transmitted intensity of the measurement beam path in such a way that the decrease in radiation intensity due to absorption leads to an increase in sensitivity and compensates for temperature influences on the signal, and a display for displaying and/or transmitting a value associated with the calculated quotient. In this manner, the lock-in amplifier may be self-synchronising and/or may comprise a synchronisation device for synchronising the lock-in amplifier with the chopper disc.

Figure 2:
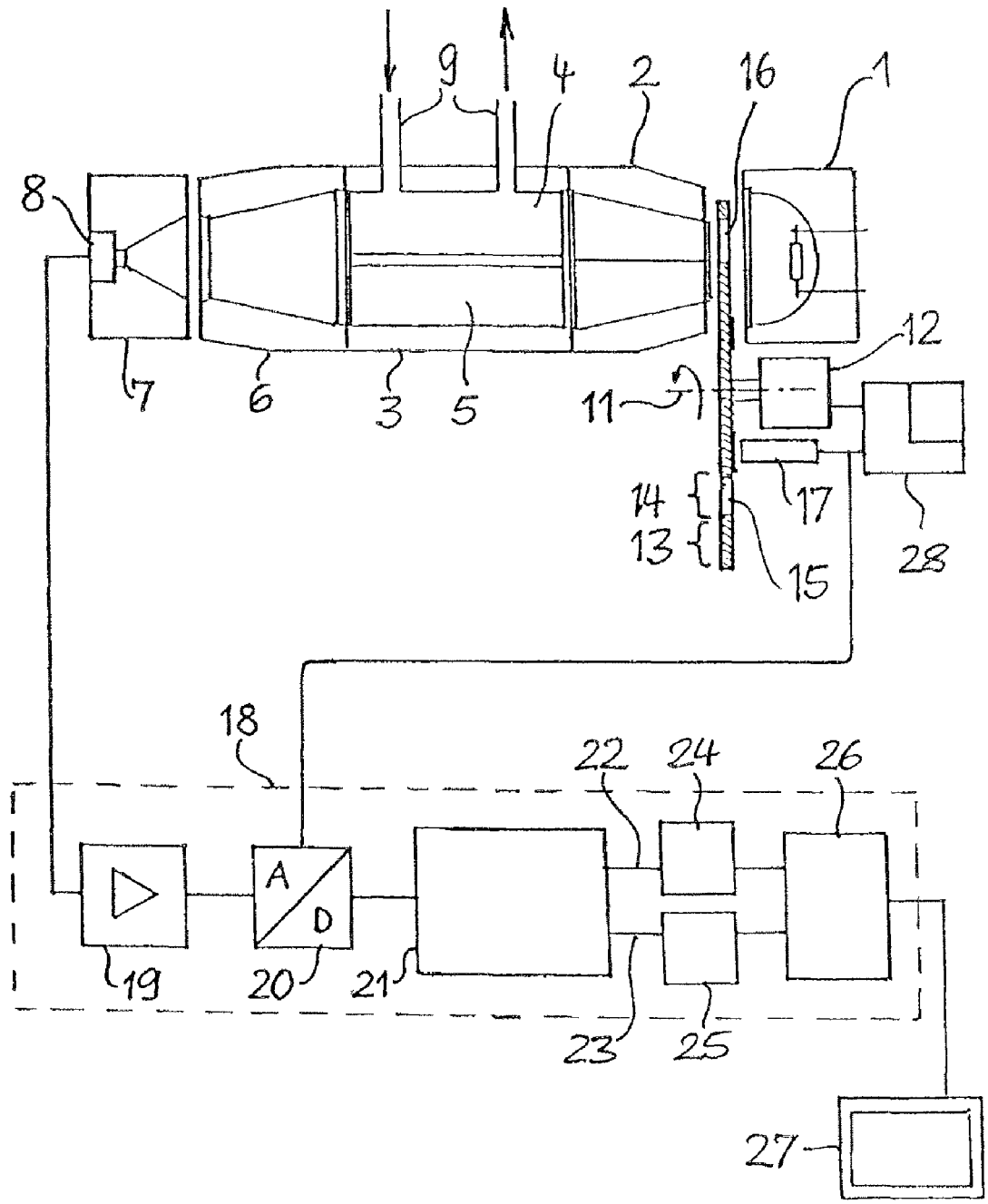

The invention will be described in greater detail hereinafter with reference to an embodiment. In the drawings:

FIG. 1 is a longitudinal cross-section through the optical part of a gas analysis device according to the invention and a block diagram of the processing of the electronic signal and FIG. 2 shows a variant embodiment of the gas analysis device according to FIG. 1.

The optical part of the gas analysis device comprises a radiator 1, a split filter cell 2, a measuring cell 3, which is separated into a measuring chamber 4 and a reference chamber 5, a filter cell 6 and a detector 7 with a photoelectric converter 8. The radiator 1 may be configured so as to generate infrared, visible or ultraviolet radiation depending on the application. The measuring chamber 4 of the measuring cell 3 is provided with connection lines 9 for supplying and removing gas samples. The reference chamber 5 and the filter cells 2 and 6 are permanently filled with suitable gases for the respective application.

Between the radiator 1 and the filter cell 2 a chopper disc 10 is arranged which is rotatable about an axis 11 and may be driven by a motor 12 having a constant rotational speed. The chopper disc 10 has two concentric, annular regions 13 and 14. The outer region 13 lies in the measurement beam path directed at the measuring chamber and the inner region 14 lies in the reference beam path directed at the reference chamber. Both regions 13 and 14 are provided with a number of openings 15, 16 arranged at equal distances from one another which are separated by closed portions shadowing the beam path. The openings 15, 16 are shaped as annular sectors. The size of the openings is dimensioned in such a way that the sum of the central angle of the openings 15 of the outer region 13 is equal to the sum of the central angle of the openings 16 of the inner region 14. The number of openings 15, 16 is, however, different in the two regions 13, 14. For example, there may be five openings 15 provided in the region 13 and four openings 16 provided in the region 14. The chopper disc 10 further comprises a rotational angle transmitter which is sensed by a sensor 17. The sensor signal is processed so as to detect the angular velocity of a time-controlled control device 28 which keeps the rotational speed of the motor 10 constant at an adjustable value. The synchronisation may, however, also be achieved from the signal itself in such a way that a synchronisation device with a sensor is not needed.

In order to process the electrical signal generated by the converter 8, an electronic signal processor 18 is connected to the converter 8, which processor substantially comprises a preamplifier 19, an analogue-to-digital converter 20, a digital lock-in amplifier 21 with algorithms which may be carried out in time-division multiplexing, adjustment and normalisation elements 24, 25 and an evaluation calculator 26. The digital signal emitted by the evaluation calculator 26 is displayed in a display device 27 and/or transmitted to data collection systems.

The described gas analysis device functions as follows:

The light emitted from the radiator 1 is directed from the chopper disc 10 rotating with a constant angular velocity into the measuring chamber 4 with a first frequency modulated by the openings 15 and into the reference chamber 5 with a second frequency modulated by the openings 16. The detector 7 detects the transmitted radiation intensity of the sample arranged in the measuring chamber and the radiation intensity of the reference sample arranged in the reference chamber with the respective modulated frequencies.

The converter 8 of the detector 7 generates an electrical mixed signal corresponding to the radiation intensity being received, which mixed signal is composed of the two frequency portions. The mixed signal is amplified by the preamplifier 19 and is converted in the A/D converter 20 into a digital mixed signal supplied to the digital lock-in amplifier 21. During digitalisation, a constant sampling frequency is used which, together with the frequencies of the measurement and reference signals, leads to mixed frequencies. The sampling frequency of the A/D converter 20 should be at least 2.5 times greater than the greatest signal frequency generated by the rotation of the chopper disc 10; preferably, a high sampling frequency is selected. In order to avoid beats in the mixed frequencies, an asynchronous sampling frequency may be used. In this case, the asynchronous sampling frequency must have a frequency distance from the frequencies of the chopper disc and the integer multiples of the frequencies of the chopper disc which is greater than the bandwidth of the measurement, i.e. the asynchronicity must be selected in such a way that the mixed frequencies are averaged out from the measurement results.

The digital lock-in amplifier contains a processing unit, for example a signal processing processor, which carries out various mathematical operations either simultaneously or at least in quick succession in a time-shared manner. The lock-in amplifier is programmed in such a way that the signal portions contained in the supplied digital mixed signal are separated in accordance with their respective frequencies. Consequently, the phase position and frequency of the signal portion corresponding to the reference signal are defined in accordance with a first algorithm from the mixed signal by comparison with the sine frequency underlying the reference signal. The phase position and frequency of the signal portion of the mixed signal corresponding to the measurement signal are derived according to a second algorithm from the phase position and frequency of the reference signal. This has the advantage that the phase of the measurement signal may also be monitored if the measurement signal is very small due to high absorption. In the described manner, the signal portions contained in the mixed signal are separated into a measurement signal and a reference signal in accordance with their respective frequencies. An output 22 of the lock-in amplifier 21 thus delivers a measurement signal which corresponds to the radiation intensity transmitted by the sample and the second output 23 of the lock-in amplifier 21 delivers a reference signal which corresponds to the radiation intensity transmitted by the reference sample. The measurement and reference signals are adjusted and normalised with an adjustable correction factor in the subsequent adjustment and normalisation elements 24, 25 in order to balance out any slight differences which may be present in the temperature path between the measurement and reference sides in such a way that the quotient of the reference signal in the numerator and the measurement signal in the denominator results in the value one. The quotient and the zero-point correction are calculated in the evaluation calculator 26 which can also make further corrections to the signal in order to balance out pressure differences and cross-sensitivity.

In the variant shown in FIG. 2 of the gas analysis device according to FIG. 1, the rotational angle signal of the chopper disc 10 detected by the sensor 17 is supplied to the A/D converter 20. In this case the A/D converter 20 is configured in such a way that the analogue mixed signal from the preamplifier 19 is digitally sampled at the same time as the frequency of the chopper disc 10. During said synchronous sampling, signal beats are avoided and the accuracy of signal processing can be further increased. In any case, it should be ensured that the sampling frequency and chopper disc frequency are not displaced, i.e. that no jitter occurs, since even minimal displacements of the frequencies may lead to the signal being corrupted. The digital mixed signal is further processed in the lock-in amplifier 21 and the subsequent components of the electronic signal processor 18 as described above.

The invention claimed is:

1. A method for measuring optical absorption of samples, comprising:
   directing light from a radiation source at a sample to be examined and at a reference sample;
   modulating the light transmitting the sample to be examined with a first frequency and modulating the light transmitting the reference sample with a second frequency, the first frequency being different from the second frequency;
   converting the radiation intensity transmitted from the sample to be examined and from the reference sample into an electrical mixed signal via a photoelectric converter;
   increasing the electrical mixed signal in a pre-amplifier;
   converting the increased electrical mixed signal into a digital mixed signal in an analogue-to-digital converter;
   separating the digital mixed signal, with regard to the first frequency, into a measurement signal associated with the sample to be examined and, with regard to the second frequency, into a reference signal associated with the reference sample using a digital lock-in amplifier; and
   forming a quotient from the reference signal and the measurement signal as a measurement for the concentration of the sample to be examined in such a way that the reduction in the intensity of the radiation due to absorption leads to an increase in sensitivity.

2. The method according to claim 1, wherein phase position and frequency of the portion of the mixed signal corresponding to the reference signal are defined from the mixed signal by means of comparison with a sine frequency underlying the reference signal, and phase position and frequency of the portion of the mixed signal corresponding to the measurement signal are deduced from the phase position and frequency of the reference signal.

3. The method according to claim 2, wherein an asynchronous sampling frequency is used during digitalisation.

4. The method according to claim 1, wherein the digital sampling of the analogue mixed signal is carried out synchronously with the frequency of a chopper disc for modulating the first and second frequencies.

5. The method according to claim 1, wherein the temperature-dependent influences on the measurement signal and the reference signal are balanced out separately for each of the two signals.

6. The method according to claim 1, wherein temperature-dependent influences on the measurement signal and the reference signal are balanced out together for both signals in a normalisation element.

7. The method according to claim 1, wherein when measuring the sample face using zero test gas the measurement signal is adjusted via a variable correction factor of the evaluation circuit in such a way that the quotient of the measurement signal and reference signal is one.

8. An apparatus for measuring optical absorption of samples, comprising:
   a light source;
   a photoelectric converter;
   a measurement beam path arranged between the light source and the converter, in which path the sample to be examined is arranged,
   a reference beam path arranged between the light source and the converter, in which path a reference sample is arranged,
   a motor-driven chopper disc with a first number of first openings unblocking only the path for the measurement beam and a second number of second openings unblocking only the path for the reference beam, the first number of first openings being different from the second number of second openings;
   a digital lock-in amplifier connected to the converter, the lock-in amplifier being designed to separate the signals received from the converter, with regard to a first frequency, into a measurement signal associated with the measurement beam path and, with regard to a second frequency, into a reference signal associated with the reference beam path; and
   an evaluation circuit for forming a quotient from the transmitted intensity of the reference beam path detected by the converter and the transmitted intensity of the measurement beam path detected by the converter as a measurement for the concentration of the sample.

9. The apparatus according to claim 8, wherein the lock-in amplifier is self-synchronising.

10. The apparatus according to claim 8, further comprising an analogue-to-digital converter connected to a synchronisation device for synchronising the digital scanning of the analogue mixed signal with the chopper disc.

11. The apparatus according to claim 8, further comprising an adjustment and normalisation device for balancing out differences in a temperature path between the reference and the measurement signals.

12. The apparatus according to claim 8, wherein the evaluation circuit is configured so as to compensate for differences in pressure and/or cross-sensitivity and/or so as to further linearize and/or offset temperature in the deflection.

13. The apparatus according to claim 8, further comprising a device for displaying and/or transmitting the ascertained concentration of the sample.

* * * * *